(12) United States Patent
Lee

(10) Patent No.: US 6,306,385 B1
(45) Date of Patent: Oct. 23, 2001

(54) METHOD OF PROTECTING AGAINST CHRONIC INFECTIONS

(76) Inventor: Eng-Hong Lee, RR#4 Rockwood, Octario (CA), N0B 2K0

(*) Notice: Subject to any disclaimer, the term of this patent is extended or adjusted under 35 U.S.C. 154(b) by 0 days.

(21) Appl. No.: 09/062,316

(22) Filed: Apr. 20, 1998

(51) Int. Cl.⁷ .................... A01N 63/00; A01N 65/00; A61K 39/00; A61K 35/12; C12N 1/00
(52) U.S. Cl. .................... 424/93.1; 424/93.7; 424/184.1; 424/520; 435/243
(58) Field of Search ................ 424/184.1, 93.1, 424/93.7, 184, 520; 435/243

(56) References Cited

U.S. PATENT DOCUMENTS

| | | |
|---|---|---|
| 4,935,007 | 6/1990 | Bafundo . |
| 5,187,080 * | 2/1993 | Andrews et al. . |
| 5,968,914 * | 10/1999 | von Borstel et al. . |

FOREIGN PATENT DOCUMENTS

| | | |
|---|---|---|
| 2098773 | 12/1994 | (CA) . |
| 0 243 548 | 11/1987 | (EP) . |
| 0 258 045 | 3/1988 | (EP) . |
| WO 93 01276 | 1/1993 | (WO) . |
| WO 96 25951 | 8/1996 | (WO) . |

OTHER PUBLICATIONS

Scheller et al (PNAS USA, vol. 92, pp. 4066–4068), Apr. 1995.*
Crane et al (Infection & Immunity vol. 59(4) pp 1271–1277), Apr. 1991.*
Chapman (Poultry Science vol. 73 (3) pp. 476–478), Mar. 1994.*
Chemical Abstracts, vol. 122, No. 23, Jun. 5, 1995 Columbus, Ohio, US; abstract No. 281737, K. Munir et al.: "Immunodilatory Effects of Salinomycin Sodium in Broiler Chickes" XP002087567 see abstract & K. Munir et al: "Immunodilatory Effects of Salinomyci Sodium in Broiler Chickes" Pak. Vet. J. vol, 14, No. 4, 1994, pp. 171–179, Lahore, Pakistan.

Chemical Abstracts, vol. 112, No. 7, Feb. 12, 1990 Columbus, Ohio, US; abstract No. 48277, M. Mazurkiewcz et al.: "Studies on Pathochemism in the Negative Interaction Between Tiamulin and Ionophoric Anticoccidials in Broilers" XP002087568 see abstract & M Mazurkiewicz et al.: "Studies On Pathochemism in the Negativ Interaction Between Timulin and Ionophoric Anticoccidials in Broilers" Colloq. Inra, 1989, pp. 273–278.

Chemical Abstracts, vol. 128, No. 24, Jun. 15, 1998 Columbus, Ohio, US; abstract No. 289787, Mariya Khalacheva et al.: "Anticoccidial Efficiency of Some Ionophore Drugs" XP002087569 see abstract & M. Khalacheva et al.: "Anticoccidial Efficiency of Som Ionophore Drugs" Vet. Med., vol. 2, No. 3, 1996, pp.157–158, SOFIA.

* cited by examiner

*Primary Examiner*—Mark Navarro

(57) ABSTRACT

The present invention is directed to a method of protecting an animal against a chronic disease, the disease being caused by an infectious organism which undergoes more than one life cycle. The method comprises:

a) administering to the animal a vaccine containing sufficient organisms to develop an immunological response in the animal;

b) maintaining the animal free from chemotherapeutic agents effective against the infectious organism for a period of time corresponding to about one life cycle of the organism; and c) thereafter administering to the animal a chemotherapeutic agent effective against the infectious organism for a period of time corresponding to at least one life cycle of the infectious organism.

16 Claims, No Drawings

METHOD OF PROTECTING AGAINST CHRONIC INFECTIONS

FIELD OF THE INVENTION

The present invention is directed to a method of protecting animals against chronic infections, particularly, a method for protecting poultry flocks against chronic infections, in particular, coccidiosis.

BACKGROUND OF THE INVENTION

There are many diseases of importance in animal husbandry which are caused by chronic infectious agents which go through more than one life cycle during the infection. Many of these diseases are of financial importance to the owner of the animals, as many such diseases can cause effects to the animals which may not be apparent until the animal is prepared for market. These infectious agents may be bacteria, viruses or protozoa, but all have in common the property of multiple life cycles during the infection of the animal.

Chronic infections are of most importance to animals which have a short time for growing out prior to market. For example, poultry are generally marketed within weeks after hatching and this short time period does not permit the animals sufficient time to recover from a chronic infection prior to market if not treated in time. One particular chronic infectious agent which is of importance to the management of poultry flocks is coccidiosis caused by a protozoa of the genus Eimeria. Coccidiosis is a very common disease of poultry and there are several species of Eimeria which are known to cause such disease. The symptoms and severity of the disease are dependent upon the species of Eimeria with which the bird is infected with *E.tenella, E.acervulina* and *E.maxima* being three of the most prevalent species. Presently, poultry flocks are protected against coccidiosis by either immunization or the use of anti-coccidial chemotherapeutic agents with the most commonly utilized method for controlling coccidial infections being the use of anti-coccidial agents.

Such anti-coccidial agents are commonly ionophores, a class of antibiotics of complex structure although other chemotherapeutic agents are also used. Many such ionophores exhibit anti-coccidial activity, although the relative degree of activity varies from one agent to another. The ionophores which are commonly utilized for commercial control of coccidiosis include monensin, narasin, lasalocid and salinomycin. If anti-coccidial agents such as ionophores are utilized for control of coccidiosis in animals, it is necessary that the agent be continuously administered to the animal typically by being mixed with the feed used for raising the animal. Another problem associated with the use of anti-coccidial therapeutic agents is the possibility of resistant strains of Eimeria developing as a result of exposure to the anti-coccidial agent. There have, in fact, been reports of such resistant strains developing in the field.

As noted above, another method of controlling chronic infections, especially within poultry, is the use of immunization. At the present time, poultry hatchlings, within the first few days of life, are immunized against various diseases and the type of vaccine used for each disease dictates its method of administration. Attenuated vaccines are usually administered in the hatchery by injection at the time of sorting of the hatchlings from the hatching incubator into holding or transporting trays. Live vaccines are more commonly administered once the hatchlings are established in their brooding trays in the form of aqueous suspensions either sprayed on feed, added to the drinking water or the use of gelled form of vaccines such as taught in my PCT Application WO 96/25951 published Aug. 29, 1996.

Coccidiosis vaccines are at present comprised of live virulent strains of coccidia in a suitable carrier for administration, the coccidia being capable of causing a mild form of the disease and selected to be very anticoccidial susceptible.

Immunization does have some drawbacks, in that there may be antigenic diversity amongst species of the infectious agent as well as amongst strains of a particular species of the infectious agent. Thus, depending upon the antigenic diversity displayed in a field strain of the organism, immunization may not be quite so effective against that particular strain. In addition, organisms may undergo antigenic mutation to the point where the immunological response induced as a result of the immunization will not have sufficient specificity against the antigens present on the field strain to protect the animal against infection by the field strain. Use of live vaccines also results in the induction of a mild disease state in the animal from which the animal would normally recover, however, in immunosuppressed or immunoincompetent animals the degree of the disease state induced by the immunization may become significant. In such circumstances the uniformity of the therapy is affected with resultant variation in weight gain and feed conversion of the animals.

There have been attempts to overcome the above difficulty by the use of a combination of immunization and chemotherapy. U.S. Pat. No. 4,935,007, issued Jun. 19, 1990 to Eli Lilly and Company describes a method for control of coccidiosis involving both immunization and ionophore chemotherapy. The method of this patent involves orally administering to the animal at a neonate stage sufficient coccidial organisms to generate an immunological response while maintaining the animal free of any chemotherapeutic anti-coccidial. After the sporozoites have penetrated the host cells, an anti-coccidially effective dose of an ionophore is administered substantially continuously throughout the life of the animal.

While the method as described in U.S. Pat. No. 4,935,007 attempts to overcome the difficulties of the two methods of controlling coccidiosis, there are drawbacks associated with that method. The ionophore is administered to the animals commencing within 24 hours of immunization and continued throughout the life of the animal. Thus, the use of the method of U.S. Pat. No. 4,935,007 does not result in any significant savings over the traditional use of a chemotherapeutic agent alone. In addition, the commencing of the use of the chemotherapeutic agent within 24 hours of the immunization may not permit the full immunological response to occur, particularly if there are antigens which may not be expressed until later stages of the life cycle.

There thus remains a need for an improved method of controlling chronic diseases caused by infectious agents which undergo multiple life cycles in animals, and in particular, a method of controlling coccidiosis in poultry.

SUMMARY OF THE INVENTION

In one aspect, the present invention is directed to a method of protecting an animal against a chronic disease, the disease being caused by an infectious organism which undergoes more than one life cycle. The method comprises:
 a) administering to the animal a vaccine containing sufficient organisms to develop an immunological response in the animal;

b) maintaining the animal free from chemotherapeutic agents effective against the infectious organism for a period of time corresponding to about one life cycle of the organism; and c) thereafter administering to the animal a chemotherapeutic agent effective against the infectious organism for a period of time corresponding to at least one life cycle of the infectious organism.

DETAILED DESCRIPTION OF THE PREFERRED EMBODIMENTS

The present invention is directed to a method for protecting an animal against a chronic disease, the disease being caused by an infectious organism which undergoes more than one life cycle. The present invention is effective against such organisms, particularly, slowly evolving organic pathogens. Many such diseases are known and in a number of such circumstances, subsequent re-infection after the first life cycle tends to increase the extent of deleterious effects of the infection. While the present invention is suitable for use with any such slow evolving pathogens causing a chronic infection, it is particularly suitable for controlling coccidiosis in any animal susceptible to coccidiosis. Many warm blooded animals of importance to animal husbandry are susceptible to coccidiosis such as for example swine or poultry. Of these animals, it is found that poultry suffer most from coccidiosis, with chickens and turkeys being the species most commonly needing protection. Because of the prevalence of coccidiosis in chickens and turkeys and because of their economic importance, the present invention is particularly useful for controlling coccidiosis in such animals. The present invention may also be utilized with other poultry species such as duck, geese, quail, pheasants and the like, or other warm blooded animals important in animal husbandry, such as cattle, sheep, swine and the like.

The method of the present invention is practiced by first immunizing the animal by administering to the animal a vaccine containing sufficient organisms to develop an immunological response in the animal. This administration is carried out at a suitable time in the life of the animal, preferably shortly after birth or hatching. In general, the administration will be carried out within the first 24 hours after birth or hatching.

In a poultry hatchery, at the time of emergence of the hatchlings from their shells in the incubation trays, they are generally examined for defects, immunized with poultry vaccines by injection and then sorted by sex and placed into holding or transporting trays. Once in the brooding trays, the chicks may be administered live vaccine by means of the watering system, by means of on feed spray or through the use of a gelled vaccine. Aqueous-based live vaccines are generally particulate in nature and if administered in the watering system, the vaccines should be provided in a composition which will maintain a relatively uniform suspension of the organisms in the vaccine. This is particularly true for coccidiosis vaccines which consist of relatively large oocysts of Eimeria species. Coccidiosis vaccines are usually administered orally for immunizing domestic animals of the avian species from coccidiosis, the vaccine having oocysts of at least one coccidium in relation to which the immunization is desired.

One common method of immunization against coccidiosis involves the use of on-feed spray administration while the birds are feeding from flats or other containers. A vaccine comprising oocysts of Eimeria species in a water based carrier is sprayed onto the feed to be provided to the hatchlings. The use of on-feed spray administration requires large doses of oocysts and uniform exposure of the flocks to the vaccine cannot always be achieved.

Vaccine may also be administered through the use of water proportioning systems including automatic fountains and automatic water medicator or proportioners. However, given the particulate nature of coccidiosis vaccines, it is doubtful that the vaccine may actually make it to the end of the water line, resulting in uneven exposure of the flock. Additionally, administration of the vaccine through the water proportioning system requires that after administration of the vaccine, the proportioning system be thoroughly cleaned to remove any residual vaccine.

The present invention in a preferred embodiment utilizes a gel form of a coccidiosis vaccine as described in my previous patent application WO 96/25951, published Aug. 29, 1996. This form of a vaccine contains the oocysts of the coccidium diluted and suspended in a gel form which results in maintaining an uniform suspension of the oocysts and consequently, relatively uniform infection of the flock by the oocysts. The gel form of the vaccine is particularly useful with Eimeria species, more particularly with *Eimeria tenella* or other species such as *Eimeria necatrix, Eimeria acervulina, Eimeria maxima, Eimeria brunetti, Eimeria praecox,* and *Eimeria mitis* are also useful. The method of obtaining each of these species is well-known by those skilled in the art. Two or more species of Eimeria can be used simultaneously and in the practice of the present invention, it is generally not necessary to use more than six species together in the same suspension.

The gel form vaccine provides for an easy to handle method of vaccinating poultry hatchlings in the hatchery and is, therefore, suitable for general hatchery workers without any special expertise required. The gel form is produced utilizing an edible polysaccharide gel, preferably a low temperature setting alginate or carrageenan gel, most preferably the kappa carrageenan gel sold as refined carrageenan Bengel MB 910, a water soluble kappa-type carrageenan extracted from the red algae *Eucheuma cottonii.*

The gel form of the vaccine is prepared by dissolving the gel powder in water at a suitable temperature to effect complete dissolution of the polysaccharide powder. The powder is added to the water at a concentration such that, when mixed with the oocyst suspension and allowed to gel, a relatively soft gel results. The dissolved gel powder and organism suspension are mixed in volumes such that the temperature of the resultant mixture is within the tolerant temperature of the organism. Typically, the dissolved gel powder and oocyst suspension are mixed in a ratio of about 1:1(v:v) to prepare the gel form of the vaccine.

The gel form vaccine has sufficient levels of the oocysts to provide immunization to the flock. It has been found that each hatchling will consume about 0.5 to 1.5 ml of the gel within a few hours and the concentration of the oocysts in the gel should be such as to provide sufficient organisms in this typical volume to immunize the hatchling. It has been found that between about 50 and 1,000 oocysts per bird provides adequate protection and so it is preferred if the gel form of the vaccine has between about 100 and 500 oocysts per ml of gel, to provide for proper immunization of the flock. Preferably, the gel form of the vaccine contains between about 200 and 300 oocysts per ml of gel, most preferably about 250 oocysts per ml of gel. As the gel form is prepared by mixing the dissolved polysaccharide powder with the oocyst suspension in equal volumes, preferably one volume of a 2 to 5% polysaccharide gel solution is mixed with an equal volume of oocyst suspension containing between about 200 and 1,000 oocysts per ml, more preferably one volume of a 2 to 4 percent polysaccharide solution with an equal volume of oocyst suspension containing between about 400 and 600 oocysts per ml, most preferably a 2.5 percent solution of polysaccharide is mixed with an equal volume of oocyst suspension containing about 500 oocysts per ml.

The use of the edible polysaccharide gels results in a gel which forms very rapidly, usually in less than an hour and preferably within about 3 to 5 minutes at 4° C., maintains the vaccine organisms in uniform suspension and allows for more uniform exposure of the poultry hatchlings to the vaccine organisms. The low content of the edible gum in the gel form means that approximately 95 percent or more of the gel form is water which can aid in the hydration of the bird and induce the feeding response. The gel form has other advantages over liquid suspensions in that the gel form will not wet the bird and therefore will not affect the health of the chicks, particularly in winter when, if the hatchling becomes wet through exposure to aqueous solution, the exposure may cause death of the hatchling. The use of the edible polysaccharide gel which gels at a relatively low temperature is also suitable for adding nitrogen nutrients and other additives such as vitamins to the gel form or competitive exclusion products such as BROILACT sold by Orion Corp., Finland. This is especially useful with heat sensitive nutrients which, if exposed to temperatures over about 50° C., are denatured. The use of the gel form vaccine also realizes a saving in the hatchery in that as the gel form is 95 percent or more water, additional watering systems are not needed such as a built-in watering system. This reduces the likelihood of the spilling of water and wetting of the chicks which can affect the health of the birds.

In the past, treatment of chronic diseases caused by an infectious organism may have involved multiple doses of the vaccine. Although it is possible that the administration of the effective organisms may be in more than one dose, when practicing the present invention, for most organisms there are no advantages to multiple dosing and a single dose is generally sufficient.

When practicing the method of the present invention, it is possible to rely on recycling of the organism to provide for multiple exposures of the animals to the organism. This is particularly true in the case of coccidiosis in chickens where the oocysts are shed into the feces at the end of every life cycle. The chicks are thereby exposed to the shed oocysts at the end of the first life cycle, and thus are given a second dose of the organisms. A chemotherapeutic therapy is commenced just after the start of the second life cycle, or just after the animals have been exposed to the organisms which have been shed at the end of the first life cycle.

The exact number of infective organisms to be administered in the vaccine should be such to be effective to develop an immunological response in the animal. The number should be sufficient to provide a uniformly low level exposure to all animals without causing severe disease. This number would vary, depending upon the nature of the infective organism and the animal to be treated. Such factors may include the species and size of the animal, the relative immunogenicity of the infective organism being administered in the vaccine, the nature of the vaccine, whether the organism is developed from a wild strain or an attenuated strain, and other factors known to those of skill in the art. The suitable number of organisms sufficient to develop the immunological response in the animal may be easily determined by those of ordinary skill in the art through the use of common techniques for vaccine development.

After the infectious organism is administered to the animal, the animal is left to be exposed to the entire antigenic complement of the organism to enable it to develop the full immunological response to the infective organism before the commencement of chemotherapy. Generally, the period of time between administration of the infective organism and the commencement of chemotherapy would correspond to about one life cycle of the infective organism. This will enable the animal to be exposed to the full antigenic complement of the infective organism, particularly for those infective organisms which go through various stages in the life cycle. For example, an Eimeria species will go through a number of stages in the life cycle such as sporulated oocysts, sporozoites and sporocysts. The antigenic complement presented to the animal during each of these stages may be different and it is of advantage to the development of the immunological response that the animal be exposed to the full antigenic complement. In a preferred embodiment of the present invention, the administration of the chemotherapeutic agent is commenced during the early part of the second life cycle and continued to about the end of the third life cycle. By commencing the chemotherapeutic agent treatment during the second life cycle, this allows recycling to occur in the animal, such that they are exposed to the organisms shed at the end of the first life cycle. However, the subsequent stages in the recycling, such as the exposure at the end of the first life cycle is not as uniform as the exposure to the controlled dosages and the vaccine. Consequently, the effects of such exposure are more variable. For Eimeria species, one life cycle takes approximately 5 to 9 days, with major species having life cycles of 5 to 7 days, E. tenella having a life cycle of 6 to 7 days. Thus, in practicing the present method for controlling coccidial infections in poultry, within about 10 days after administering the vaccine, chemotherapy is begun by administering the suitable chemotherapeutic agent effective against the infective organisms.

The nature of the chemotherapeutic agent will depend upon the chronic disease and the nature of the infectious organisms, as well as on the species of the animal being treated. The selection of the chemotherapeutic agent and the amount to be administered is generally similar to traditional chemotherapy regimes for treatment of such diseases in the particular species of animals.

For example, for the control of coccidiosis in poultry, ionophores such as monensin, narasin, lasalocid, and salinomycin are commonly utilized and any of these may be employed in the present invention. A number of other ionophores that may also be utilized include laidlomycin, nigericin, grisorixin, dianemycin, lenoremycin, lonomycin, antibiotic X206, albroixin, septamycin, antibiotic A204, etheromycin, isolasalocid, antibiotic A23187, maduramicion, and many others. In addition, non-ionophore chemotherapeutic agents such as amprolium, diclazupil, clopidol, decoquinate, narasin, nicarbazin, robenidine, halofuginone, and zoalene may also be used. The ionophore anti-coccidial chemotherapeutic agents are preferred.

The chemotherapeutic agent is generally administered to the animal for a period of time corresponding to at least about one life cycle of the infectious organism. The main function of the administration of the chemotherapeutic agent is to limit the effects to the animal from the live vaccine, particularly, effects evident after the first life cycle of the infectious organism. By administering the chemotherapeutic agent at this time, the second and subsequent life cycles which generally are not as uniform in exposure in terms of time and dose of exposure are controlled. Such subsequent life cycles may also cause cumulative effects which may cause more damage to the animal. This enables mitigation of any possible side effects of vaccination, while permitting the full immunological response of the animal to the vaccination to develop.

Depending upon the nature of the infectious agent, the nature of the disease and the species of animal being treated, the chemotherapeutic agent will be administered to the animal for one or more such life cycles. Thus, in some circumstances, it may only be necessary to administer the chemotherapeutic agent to the animal for a period of time corresponding to one life cycle of the infectious organism. After that time, the continuation of chemotherapy is no longer necessary. In other circumstances, it may be necessary to maintain the animal on the chemotherapeutic agent for a period of time corresponding to more than one life cycle of the infectious organism, perhaps for a period of time corresponding to two or three life cycles of the infectious organisms.

In particular, for control of coccidiosis in poultry, in most circumstances, it is only necessary to maintain the animals on the chemotherapeutic agent for a period of time corresponding to at least one life cycle of the coccidial organism, preferably for a period of 10 to 14 days. After this time, the birds are immunized and the medication is no longer needed for protection.

In some circumstances, such as for example where the birds are being exposed to a particularly virulent field strain, it is preferable to maintain the animals on the chemotherapeutic agent for a period of time corresponding to about two life cycles of the organism. Thus, for example when the method is used to control coccidiosis in poultry, the birds will be maintained on the chemotherapeutic agent for a period of about 20 to 30 days. After this period of time, the chemotherapy is discontinued and the animals are maintained on a non-medicated feed.

Another situation where it may be preferred to maintain the animals on the chemotherapeutic agent for a longer period of time is when the therapy is first introduced to the farm. For example, in some circumstances, when first introducing the therapy to a particular farm, the full effectiveness of the therapy may not be achieved until a number of flocks of the poultry have been reared on the therapeutic program. This may be particularly evident when the therapy is being utilized for field replacement of naturally occurring strains or where the naturally occurring strains of the organism may be particularly virulent. In these circumstances, it has been found useful to initially provide the chemotherapeutic agent for an extended period of time for the first flock. For each of the subsequent flocks, the chemotherapeutic treatment time is gradually reduced until the agent is only being administered for about the one life cycle. For example, for the first flock, the chemotherapy is commenced days post immunization and maintained until about one week before the birds will be marketed. For the second flock, the birds are medicated until two weeks before market, the third flock until three weeks before market, etc. This program of gradual reduction in the medication or chemotherapeutic period is continued until the chemotherapeutic agent is being administered for only the preferred time period of 10 to 14 days.

The administration of the chemotherapeutic agent follows the methods of administration commonly employed in the art. Typically, the chemotherapeutic agent is administered to the animal as an additive to the feed on which the animal is raised, i.e. by using a medicated feed. Alternatively, for some chemotherapeutic agents, they may be administered through the drinking water.

While in most circumstances a single chemotherapeutic agent is utilized in the chemotherapy treatment, there may be circumstances where mixtures of more than one such chemotherapeutic agent may also be employed.

The method of the present invention also has particular utility for replacement of the naturally occurring strains of organism in the field by a particularly selected organism. As the method of the present invention utilizes a live vaccine, for at least the first life cycle of the organism, viable organisms will be shed from the animals into the environment in which the animal is located. Over a period of a number of generations of the animal in the same location, the proportion of such organisms shed as a result of the immunization scheme in the total population of organisms present in the environment will increase until substantially most or all of the organisms in the environment are present as a result of the immunization process. In this way, the nature of the organisms in the environment may be controlled to select for organisms having a particular property, such as increased susceptibility to chemotherapeutic agents.

The method of the present invention is also adaptable to the nature of the organism found in the natural environment in which the animals are located. By utilizing standard techniques, the organisms native to the environment may be isolated and identified. Once the organism is isolated and identified, vaccines specific for the organisms and the particular strains present in the environment may be prepared to maximize the protection of the animal to the organisms found in the environment. For example, if it is found that on a particular poultry farm, *E. tenella* is the major species of Eimeria present, then the vaccine could be adjusted to have *E. tenella* as the major component of the vaccine. The particular strain of the *E. tenella* present on the local farm could also be utilized for the preparation of the specific vaccine. The organisms utilized in the vaccine could also be modified to provide for increased susceptibility to chemotherapeutic agents. In this way, the protection of the animal is maximized as the animal is being immunized against the species and strains of organisms found in the natural environment as well as over a number of generations the wild type strain present in the environment will be gradually replaced by the strain utilized in the vaccine.

In addition, the vaccine may also contain organisms which have been genetically engineered to optimize the protection of the animal to the organisms to which the animal would be exposed in the natural environment. For example, if a particularly virulent strain of the organism is present in the natural environment, the organism for the vaccine could be engineered to utilize a less virulent species or strain of the organism, the less virulent species or strain of the organism in the vaccine also being capable of expressing antigens on its surface which cross-react with, or are specific for the more virulent strain found in the natural environment. This would optimize the protection of the animal to the strain found in the natural environment while minimizing the effects of the vaccine on the animal.

The method of the present invention is illustrated in the following examples but the invention is not limited thereto. In all of the examples where it is stated that the animals were exposed to oocysts, it should be understood that the vaccine being the oocysts in the gel form was not fed to the bird manually, the birds were simply placed in the same area as the gel form vaccine during the time period and were allowed to consume the vaccine voluntarily. *Eimeria tenella* and *Eimeria necatrix* are used in the example because they are the two most pathogenic species among the six commonly found coccidia which causes coccidiosis in chickens.

They are, however, the two least immunogenic species, that is, they produce the least protection against immunization. Hence, if an immunization method is effective against *Eimeria tenella* or *Eimeria necatrix*, it would be effective for the remaining species. *Eimeria tenella* is the preferred species for experimentation partly because it is more prevalent than *Eimeria necatrix* and is the main cause of death among chickens suffering from coccidiosis. In addition, because *Eimeria tenella* appears almost exclusively in the ceca of chickens instead of infecting all over the intestines, like other species, the damage or lesions can be accurately scored.

EXAMPLE 1

A gel form vaccine was prepared by first adding 200 ml of hot tap water to 5 gm of kappa carrageenan Bengel MB 910 in a container and mixing until the MB 910 had dissolved. To this solution was added 200 ml of a solution containing 500 oocysts per ml of a mixture of *Eimeria acervulina*, *E.maxima* and *E.tenella* and the combined solution was mixed. The solution was then poured into a plastic watering dish and allowed to cool and gel at 4° C. This resulted in a gel form of the vaccine containing 1.25 percent MB 910 and 250 oocysts per ml.

EXAMPLE 2

A paired-barn comparison was conducted between use of a anticoccidial ionophore and the method of the present invention for protecting poultry against coccidiosis. 51,000 birds were divided into two groups. One group was maintained on feed containing 60 mg per kilogram of feed of salinomycin sodium COXISTAC (Phizer). The second group was administered the vaccine prepared in accordance with Example 1 on Day 1. These birds were maintained on feed with no medication for 10 days. Thereafter, 60 mg per kilogram of salinomycin sodium was utilized in the feed for a further 10 days after which the animals were maintained on non-medicated feed until shipping. A virginiamysin based growth promotant STAFAC (SmithKline Beecham) at a level of 11 mg per kilogram of feed was used as a growth promotant in both groups. The results are for both groups and the comparison between them as shown in Table 1.

TABLE 1

| Particulars | Vaccine/Salinomycin | Salinomycin |
| --- | --- | --- |
| No. of birds placed | 25,500 | 22,950 |
| No. birds shipped | 23,334 | 21,582 |
| Market Age | 42 days | 42 days |
|  | 52 days | 52 days |
| Liveability (%) | 91.5 | 91.8 |
| Avg. Weight (kg) | 2.81 kg | 2.72 kg |
| Feed Conversion Ratio | 2.16 | 2.16 |
| EEF | 2.29 | 2.23 |

*Flock was reared for 10 days after vaccination with no medication in the feed.
Salinomycin was included in the feed for the next 10 days.

$$EEF = \text{European Efficiency Factor} = \frac{\%\ \text{Liveability} \times \text{Avg. Market Weight}}{FCR \times \text{Market Age}}$$

From the above, it can be seen that the use of the combined vaccination and the coccidial treatment resulted in a higher efficiency as measured by the European Efficiency Factor which is related to the percent liveability, average market weight, feed conversion rate and market age of the birds.

EXAMPLE 3

The above example was repeated comparing vaccine/monensin treatment with monensin alone and the results from this are shown in Table 2.

TABLE 2

| Particulars | Vaccine/Monesin | Monesin |
| --- | --- | --- |
| No. of birds placed | 22,950 | 22,950 |
| No. birds shipped | 21,352 | 21,582 |
| Sex | Cockerels | Cockerels |
| Market Age | 34 days | 47 days |
|  | 51.5 days |  |
| Liveability (%) | 93.04 | 94.1 |
| Avg. Weight (kg) | avg. - 2.78 kg | 244 kg |
|  | 45 days - 2.63 kg |  |
|  | 51.5 days - 2.90 kg |  |
| Feed Conversion Ratio | 2.12 | 2.19 |
| EEF | 2.60 | 2.23 |

*Flock was reared for 2 weeks after vaccination with no medication in the feed. Monesin was included in the feed for the next 2 weeks.

Once again, the use of the vaccine and anticoccidial method of the present invention resulted in a better feed conversion ratio and European Efficiency Factor.

EXAMPLE 4

The number of broiler/roaster crops were raised on either anticoccidial monensin alone, immunization alone or combined immunization/monensin method of the present invention. The results of these are shown in Table 3.

The present invention provides for a method of protecting an animal against a chronic disease, the disease being caused by an infectious organism which undergoes more than one life cycle. The method of the present invention is particularly effective for treating poultry flocks against chronic infections in particular, against coccidiosis infection. The method of the present invention helps to overcome some of the drawbacks of each of the individual methods namely, immunization and/or chemotherapeutic therapy by providing a means of controlling the exposure of the animal to the organism and in the preferred embodiment by controlling the nature of the organism which is found in the natural environment. This is accomplished through wild type field strain replacement by the strain utilized in the vaccine used as part of the method of the present invention.

While the present invention has been illustrated in the specific examples for use in protecting poultry, particularly chickens against coccidiosis, it is also useful for other chronic diseases. For example, the method is also usable for protecting poultry against Infectious Bursal Disease, Avian fowl Pox, Avian Encephalomyelitis, Newcastle Disease and *H. Paragallinarum* bacteria. Similarly, the method of the present invention is useful with other animals in protecting such animals against chronic diseases caused by infectious agents which recycle for more than one life cycle.

Although various preferred embodiments of the present invention have been described herein in detail, it will be appreciated by those skilled in the art, that variations may be made thereto without departing from the spirit of the invention or the scope of the appended claims.

The embodiments of the invention in which an exclusive property or privilege is claimed are defined as follows:

1. A method of protecting poultry birds against coccidiosis comprising:
   a) administering to the bird a vaccine containing sufficient live oocysts of at least one Eimeria sp. to develop an immunological response in the bird;

b) maintaining the bird free from chemotherapeutic agents effective against coccidiosis for a period of time corresponding to about one life cycle of the Eimeria sp.; and c) thereafter administering to the bird a chemotherapeutic agent effective against coccidiosis for a period of time corresponding to at least one life cycle of the Eimeria sp.

2. A method as claimed in claim 1 wherein the bird is maintained free from chemotherapeutic agents for a period of time corresponding to about two to five days beyond one life cycle of the Eimeria sp.

3. A method as claimed in claim 2 wherein the chemotherapeutic agent is administered to the bird for a period of time corresponding to about 1.5 to 2.5 life cycles of the Eimeria sp.

4. A method as claimed in claim 3 wherein the bird is maintained free from chemotherapeutic agents for about 10 days.

5. A method as claimed in claim 4 wherein the chemotherapeutic agent is administered to the bird for about 10 to 14 days.

6. A method as claimed in claim 5 wherein the chemotherapeutic agent is selected from the group consisting of monensin, narasin, lasalocid, salinomycin, laidlomycin, nigericin, grisorixin, dianemycin, lenoremycin, lonomycin, antibiotic X206, albroixin, septamycin, antibiotic A204, etheromycin, isolasalocid, antibiotic A23187, maduramicion, amprolium, diclazupil, clopidol, decoquinate, narasin, nicarbazin, robenidine, halofuginone, and zoalene.

7. A method as claimed in claim 6 wherein the chemotherapeutic agent is selected from the group consisting of monensin, narasin, lasalocid and salinomycin.

8. A method as claimed in claim 7 wherein the Eimeria sp. is one or more species selected from the group consisting of *Eimeria tenella, Eimeria necatrix, Eimeria acervulina, Eimeria maxima, Eimeria brunetti, Eimeria praecox*, and *Eimeria mitis*.

9. A method for protecting poultry birds against coccidiosis comprising:

a) administering to a first flock of birds a vaccine containing sufficient live oocysts of at least one Eimeria sp. to develop an immunological response in the bird;

b) maintaining the first flock of birds bird free from chemotherapeutic agents effective against coccidiosis for a period of time corresponding to about one life cycle of the Eimeria sp.;

c) thereafter administering to the first flock of birds a chemotherapeutic agent effective against coccidiosis until about one week before the first flock of birds are marketed;

d) repeating steps a) and b) above for each subsequent flock of birds followed by administration of the chemotherapeutic agent for a reduced period of time for each flock as compared to the immediately previous flock until the therapeutic agent is being administered to the flock of birds for a period of time corresponding to at least one life cycle of the Eimeria sp.; and e) thereafter maintaining each further flock of birds on the same program of immunization and medication.

10. A method as claimed in claim 9 wherein in step b) the birds are maintained free from chemotherapeutic agents for a period of time corresponding to about two to five days beyond one life cycle of the Eimeria sp.

11. A method as claimed in claim 10 wherein in step e) the chemotherapeutic agent is administered to the birds for a period of time corresponding to about 1.5 to 2.5 life cycles of the Eimeria sp.

12. A method as claimed in claim 11 wherein in step b) the birds are maintained free from chemotherapeutic agents for about 10 days.

13. A method as claimed in claim 12 wherein in step e) the chemotherapeutic agent is administered to the birds for about 10 to 14 days.

14. A method as claimed in claim 13 wherein the chemotherapeutic agent is selected from the group consisting of monensin, narasin, lasalocid, salinomycin, laidlomycin, nigericin, grisorixin, dianemycin, lenoremycin, lonomycin, antibiotic X206, albroixin, septamycin, antibiotic A204, etheromycin, isolasalocid, antibiotic A23187, maduramicion, amprolium, diclazupil, clopidol, decoquinate, narasin, nicarbazin, robenidine, halofuginone, and zoalene.

15. A method as claimed in claim 14 wherein the chemotherapeutic agent is selected from the group consisting of monensin, narasin, lasalocid and salinomycin.

16. A method as claimed in claim 15 wherein the Eimeria sp. is one or more species selected from the group consisting of *Eimeria tenella, Eimeria necatrix, Eimeria acervulina, Eimeria maxima, Eimeria brunetti, Eimeria praecox*, and *Eimeria mitis*.

* * * * *